(12) United States Patent
Kam et al.

(10) Patent No.: US 10,675,143 B2
(45) Date of Patent: *Jun. 9, 2020

(54) SUSPENSORY GRAFT FIXATION WITH ADJUSTABLE LOOP LENGTH

(71) Applicant: Linvatec Corporation, Largo, FL (US)

(72) Inventors: Andrew S. Kam, Odessa, FL (US);
Giuseppe Lombardo, Trinity, FL (US);
Peter C. Miller, Largo, FL (US);
Steven E. Fitts, New Port Richey, FL (US)

(73) Assignee: Linvatec Corporation, Largo, NY (US)

( * ) Notice: Subject to any disclaimer, the term of this patent is extended or adjusted under 35 U.S.C. 154(b) by 61 days.

This patent is subject to a terminal disclaimer.

(21) Appl. No.: 15/905,967

(22) Filed: Feb. 27, 2018

(65) Prior Publication Data
US 2018/0185136 A1 Jul. 5, 2018

Related U.S. Application Data

(62) Division of application No. 15/620,920, filed on Jun. 13, 2017, now Pat. No. 9,931,197, which is a division
(Continued)

(51) Int. Cl.
*A61F 2/08* (2006.01)
*A61B 17/04* (2006.01)

(52) U.S. Cl.
CPC ........ *A61F 2/0811* (2013.01); *A61B 17/0401* (2013.01); *A61B 2017/0404* (2013.01); *A61B 2017/0459* (2013.01); *A61F 2002/0817* (2013.01); *A61F 2002/0852* (2013.01); *A61F 2002/0882* (2013.01)

(58) Field of Classification Search
CPC ............ A61F 2/0811; A61F 2002/0817; A61F 2002/0852; A61F 2002/0882; A61B 2017/0459
See application file for complete search history.

(56) References Cited

U.S. PATENT DOCUMENTS

| 3,880,166 A | * | 4/1975 | Fogarty ............ A61B 17/12009 |
| | | | 606/158 |
| 5,693,060 A | * | 12/1997 | Martin ............... A61B 17/0401 |
| | | | 606/148 |

(Continued)

*Primary Examiner* — David H Willse
*Assistant Examiner* — Javier G Blanco
(74) *Attorney, Agent, or Firm* — Bond, Schoeneck & King, PLLC; Frederick J. M. Price

(57) ABSTRACT

A suspensory fixation device has an elongated anchor member adapted to be transversely situated at the exit of a bone tunnel. A graft supporting loop member formed of a pair of parallel suture limbs extending from a bight portion is suspended transversely from the anchor member and has a loop length which is adjustable so the graft ligament can be supported in the bone tunnel at varying distances from the anchor member. When a graft ligament is attached to the saddle end of the loop member, the length may be shortened by pulling distally on the pair of limbs to pull the graft ligament into the bone tunnel. When tension is applied to the loop member by the graft pulling the loop proximally, the bight portion of the suture automatically locks the graft supporting loop member in place.

4 Claims, 6 Drawing Sheets

Related U.S. Application Data of application No. 14/574,946, filed on Dec. 18, 2014, now Pat. No. 9,700,403.

(60) Provisional application No. 61/964,907, filed on Jan. 16, 2014.

(56) References Cited

U.S. PATENT DOCUMENTS

| | | | | |
|---|---|---|---|---|
| 7,594,923 | B2 * | 9/2009 | Fallin | A61B 17/0401 24/129 R |
| 2006/0293709 | A1 * | 12/2006 | Bojarski | A61B 17/0401 606/232 |
| 2008/0287991 | A1 * | 11/2008 | Fromm | A61B 17/0401 606/232 |
| 2012/0046747 | A1 * | 2/2012 | Justin | A61B 17/0401 623/13.14 |

* cited by examiner

SUSPENSORY GRAFT FIXATION WITH ADJUSTABLE LOOP LENGTH

CROSS-REFERENCE TO RELATED APPLICATIONS

This application is a division of U.S. Non-Provisional patent application Ser. No. 15/620,920 filed on Jun. 13, 2017, which is a division of and claims the benefit of priority from U.S. Non-Provisional patent application Ser. No. 14/574,946 filed Dec. 18, 2014, which claims the benefit of priority from U.S. Provisional Patent Application Ser. No. 61/964,907, entitled "Suspensory Graft Fixation with Adjustable Loop Length", and filed on Jan. 16, 2014. The content of the above-identified application is incorporated herein by reference in its entirety

BACKGROUND OF THE INVENTION

Field of the Invention

This invention relates to surgical devices for the repair and reconstruction of soft tissue injuries. In particular, this invention relates to devices and methods for the surgical implantation of replacement (autograft or allograft or artificial) ligament grafts. Still more particularly, the invention relates to the surgical repair of anterior cruciate ligament grafts.

Description of the Prior Art

The repair and reconstruction of torn or damaged soft tissues is a common surgical procedure. For example, replacement graft ligaments may be secured at the site of the original ligament. The procedure generally involves drilling bone tunnels into adjacent bones at the site of the original ligament and securing a graft ligament within these bone tunnels. In many applications, such as in the knee joint, such procedures may be performed arthroscopically. The graft ligament may be an autograft, an allograft, a xenograft, or it may be totally artificial and synthetic. Common types of anterior cruciate ligament (ACL) grafts, for example, include ones which may be autologous or allograft bone-patellar tendon-bone or soft tissue (such as semitendinosus and gracilis tendons), both types harvested by techniques well known to those skilled in the art.

The graft ligaments may be secured within the bone tunnels in a variety of ways. Of prime importance is the degree to which they can withstand pullout forces prior to complete healing. For example, it is known to use interference screws inserted parallel to the tunnel axis to compress the ends of the graft ligament against the wall of the bone tunnel to secure the graft ligament and promote tissue in-growth.

Suspensory graft fixation devices have been developed to secure a graft ligament in a bone tunnel. One such device is described in U.S. Pat. No. 8,852,250 (Lombardo et al.), entitled Graft Fixation Implant, assigned to the assignee hereof and incorporated by reference herein. Suspensory graft fixation devices work by lying transversely across the opening of a bone tunnel and generally take the form of an elongated anchor member which suspends a graft retaining loop from a fixation point on the surface of a bone to which the graft is to be attached (in this case, a femur). The elongated member has an axis and a pair of suture receiving apertures symmetrically situated on the axis on opposite sides of the center of the elongated member. In ACL procedures the elongated member, often called a button, is adapted to be situated transversely across the exit opening of the bone tunnel on the lateral femoral cortex so that a supporting loop, generally made of suture material, can be suspended from the button and can extend into the bone tunnel from the suture receiving apertures of the button. The suture loop supports one end of a graft ligament passed through the loop. The term "suture" as used herein may be any type of filamentous material such as a biocompatible or bioabsorbable filament, ribbon, tape, woven or non-woven material capable of providing the loop support and the frictional resistance required by the device described herein. In an arthroscopic procedures such as an ACL reconstruction the elongated anchor member is initially aligned with the axis of the bone tunnel, and pulled through the tunnel to the exit at the distal end on the lateral femur. For such suspensory graft fixation devices to be able to support a graft ligament and to be properly transversely situated at the exit of the bone tunnel, the suture loop and the bone tunnel must both be long enough to enable the elongated member to "flip" from an axially aligned orientation to a transverse orientation when it exits the bone tunnel.

Since the supporting loop of such a suspensory device is most often of a fixed length, graft fixation requires preparation of a graft ligament of predetermined length. Furthermore, because prior art suspensory graft fixation devices have fixed loop lengths they are produced in multiple sizes (ranging, for example, from loop lengths of 15 mm to 60 mm in 5 mm increments in the case of XO Button® implants made by ConMed Corporation, Largo, Fla.) in order to accommodate various graft and tunnel lengths that may be encountered during a surgical procedure. The fixed graft length and variations in tunnel and loop lengths make prior art suspensory ligament fixation challenging.

Recently, suspensory devices have been made with adjustable loop lengths. See, for example, U.S. patent application 2010/0256677, (Albertorio et al.) published Oct. 7, 2010 and entitled Integrated Adjustable Button-Suture-Graft Construct with Two Fixation Devices. It has been found that the adjustability of the loop length of a suspensory graft fixation device may be achieved in a manner considerably less complex than that described in the aforementioned publication.

At times surgeons may encounter situations where they cannot produce a bone tunnel of adequate length to receive a ligament graft suitable for suspensory fixation. A predetermined length of graft ligament is required to engage a predetermined portion of the bone tunnel for proper healing. For example, a so-called short tunnel ACL reconstruction may present a relatively small (narrow) femur which does not enable formation of an adequately long bone tunnel which means, in turn, the suspensory anchor member cannot be advanced far enough out of the tunnel to flip yet keep enough contact between the graft and the bone tunnel wall. Use of an adjustable loop in such situations could nevertheless enable the surgeon to proceed with a suspensory-type repair. Accordingly it is an object of this invention to produce a suspensory graft ligament repair system suitable for short tunnel repairs.

In instances in which soft tissue is to be pulled into a bone tunnel, such as ACL reconstruction, it is desired to have an adjustable loop to simplify the procedure and maximize the bone to soft tissue interface.

It is an object of this invention to produce a suspensory graft fixation device adapted to lock the size and position of the graft supporting loop after it has been set at a desired length.

It is also an object of this invention to automatically lock the graft supporting loop by pulling it in one direction relative to the anchor member, and to vary the length of the graft supporting loop, to resize it, by pulling it in the opposite direction.

SUMMARY OF THE INVENTION

These and other objects of this invention are achieved by a suspensory graft fixation device for securing a replacement ligament graft in a bone tunnel comprising an elongated anchor member adapted to be situated transversely adjacent the exit of the bone tunnel, a graft supporting element in the form of a loop adapted to support the replacement ligament graft a predetermined variable distance away from the exit, and means for adjusting the distance between the exit of the bone tunnel and the graft, and means for locking the graft supporting element to maintain the distance at a set point.

Another aspect of the invention is the method of suspensory fixation of a graft ligament comprising the steps of providing a suspensory graft fixation device as described above, providing a filamentous material to be used as a graft supporting element in the form of a loop, arranging the filamentous material in such a way as to enable it to be placed in a locking position, pulling the ends of the filamentous material in order to shorten the length of the supporting loop and locking the loop length at a desired point.

DESCRIPTION OF THE INVENTION

Figure 1:
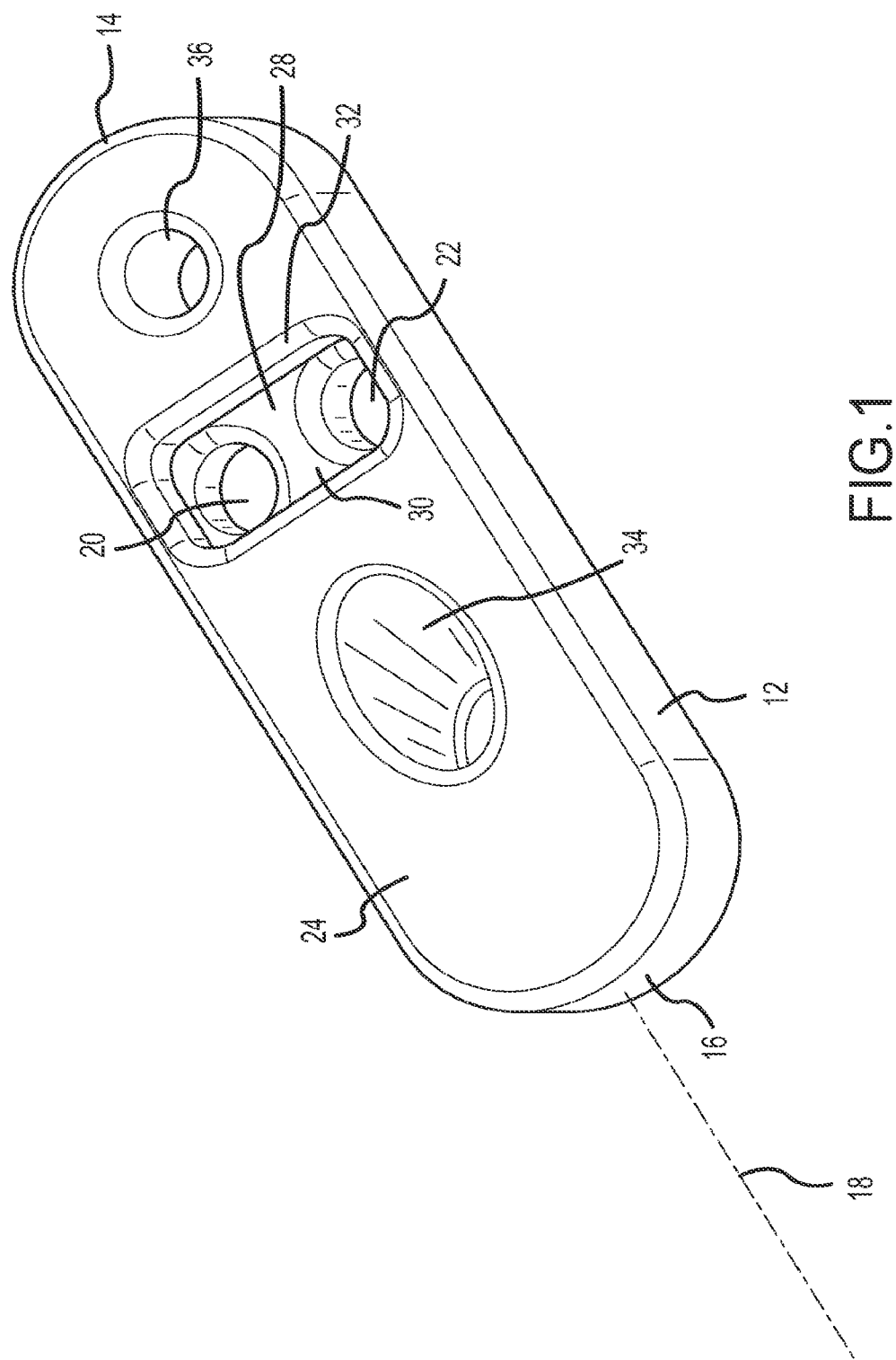
FIG. 1 is a perspective view of the anchor portion of a suspensory graft fixation device constructed in accordance with the principles of this invention.

A suspensory graft fixation device 10 constructed in accordance with the principles of this invention is shown in the drawings. Device 10 comprises an elongated anchor member 12 and suture in the form of filamentous strand 40. Anchor member 12 has a first end 14, a second end 16, an axis 18, and a pair of suture receiving apertures 20 and 22. Anchor member 12 has a top surface 24 and a bottom surface 26 (best seen in FIG. 4). Bottom surface 26 is sometimes referred to as the proximal surface and is intended to be placed adjacent a bone tunnel exit. As used herein, the term "proximal" refers to the side of the bone containing the bone tunnel (i.e., extending inwardly away from the surface of the lateral femur in an ACL procedure), and the term "distal" refers to the side of the bone against which the transverse anchor member rests (i.e., extending outwardly away from the surface on the lateral femur).

Apertures 20 and 22 are situated on opposite sides of a central bridge portion 28 extending between them. In the preferred embodiment apertures 20 and 22 are formed in a pocket/recess 30 set in top surface 24. The recess 30 has a perimeter 32 at the intersection of recess 30 with top surface 24, the purpose of which will be explained later. Anchor member 12 also has a suture return aperture 34 extending between top and bottom surfaces 24 and 26 as well as a pulling aperture 36. While one could provide one return aperture for each suture limb, in the preferred embodiment both limbs pass through one return aperture.

Device 10 is designed to have anchor member 12 operate with a filamentous strand 40 suitable for following a tortuous path through the various apertures of anchor member 12. In the preferred embodiment filamentous strand 40 is a single length of appropriately sized suture. The term "suture" as used herein may be used interchangeably with "filamentous material" and, as described above, will be understood to mean any biocompatible or bioabsorbable strand of material which can, when combined with anchor member 12, operate to support a replacement graft in the manner described below. The suture may comprise a plurality of parallel strands although in the preferred embodiment a single strand folded on itself has been found sufficient depending on size. As will be understood below, the combination of filamentous strand 40 with the features of anchor member 12 can perform different functions at different points along the path 29 of the suture through the apertures of anchor member 12.

Figure 3:
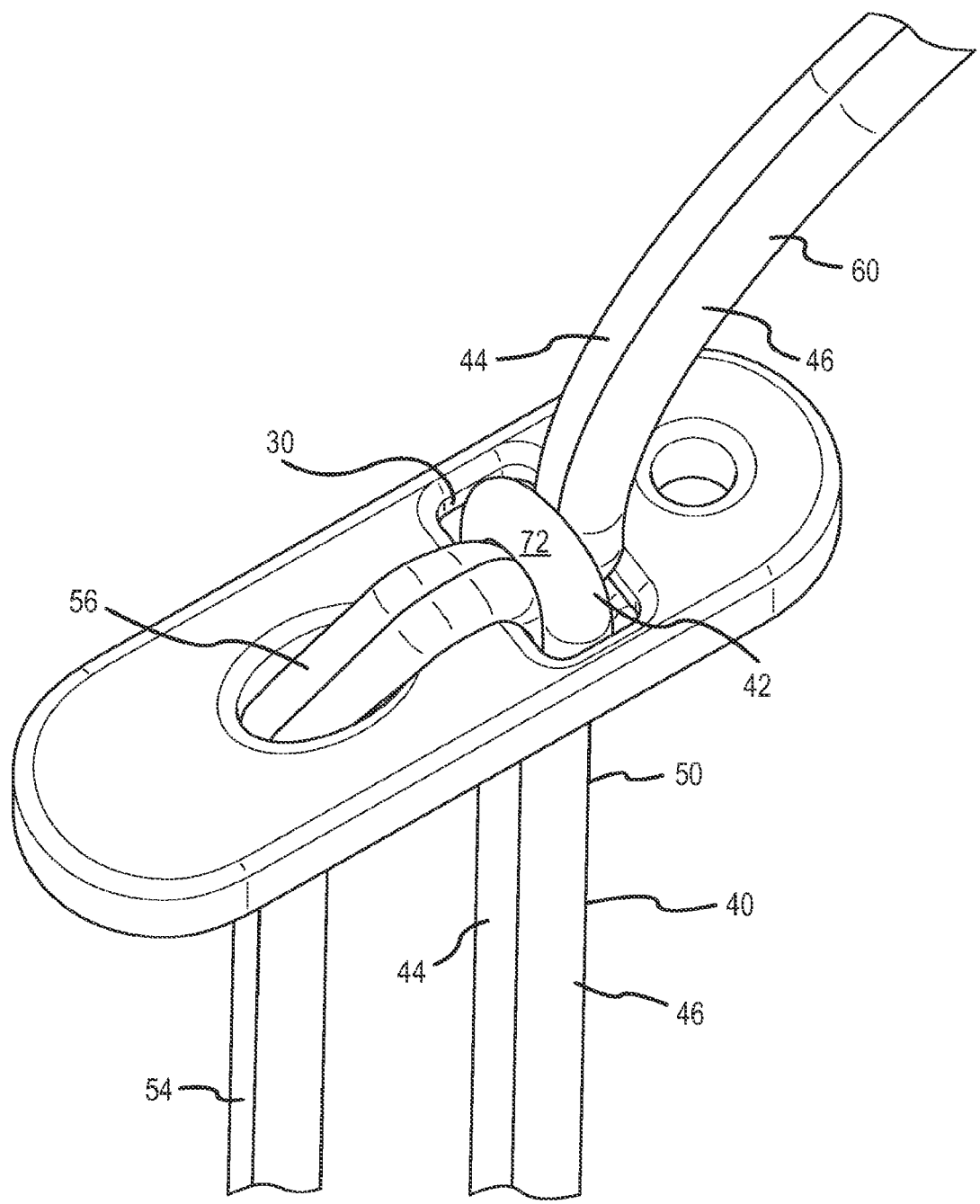
FIG. 3 is a close-up view of the suspensory graft fixation device of FIG. 2 showing the winding path of suture.

To aid in describing the winding path 29 of the filamentous material, which in the preferred embodiment is a hollow-core suture, we will start at apertures 20 and 22, and describe the various sections of path 29 through which the suture is threaded. To facilitate the explanation of winding path 29 we will define suture strand 40 as folded on itself to form a central bight portion 42, thus creating two limbs 44 and 46 extending from bight 42. Each limb has a length extending from the bight to the free, unattached end of the limb. Referring to FIG. 3, suture leg 44 is passed down through receiving aperture 20 into section 50, across the bottom of graft supporting loop 70 into section 52, up on the other side of loop 70 into section 54, up through aperture 34 into section 56, under bight 42 into section 58 and away from the anchor member 12 in section 60. Similarly, limb 46 of the suture follows a path parallel with that of limb 44 through the same sections as suture limb 44. Path 29 results in formation of locking loop 70, the length L of which is easily adjustable. The loop is created by the suture following the path of sections 50, 52, 54, 56 and 58. Loop 70 is intended to receive a graft, generally folded on itself in the case of soft tissue (not shown) suspended from section 52.

In the preferred embodiment the two loop strands forming supporting loop 70 are made of high strength, filamentous material such as ultra-high molecular weight polyethylene and anchor member 12 is comprised of implantable grade titanium.

The invention facilitates the operation of device 10 by activating a loop length adjustment mechanism to resize the graft supporting loop by applying tension to the construct in one direction (distally), and activating an automatic loop locking mechanism by applying tension to the construct in the opposite direction (proximally). In the preferred embodiment, the central bight 42 forms a locking loop 72 creating downward (as viewed in FIG. 3) pressure on the suture in section 58 due to the downward force exerted on supporting loop 70 by the graft itself (not shown) adjacent section 52. This portion of section 52 is sometimes referred to as a "saddle". Locking loop 72 pushes the suture in section 58 deeper into the pocket/recess 30 thus activating the locking mechanism which causes the suture to engage the perimeter 32 and apertures 20, 22 thereby further increasing the friction created by locking loop 72.

Figure 4:
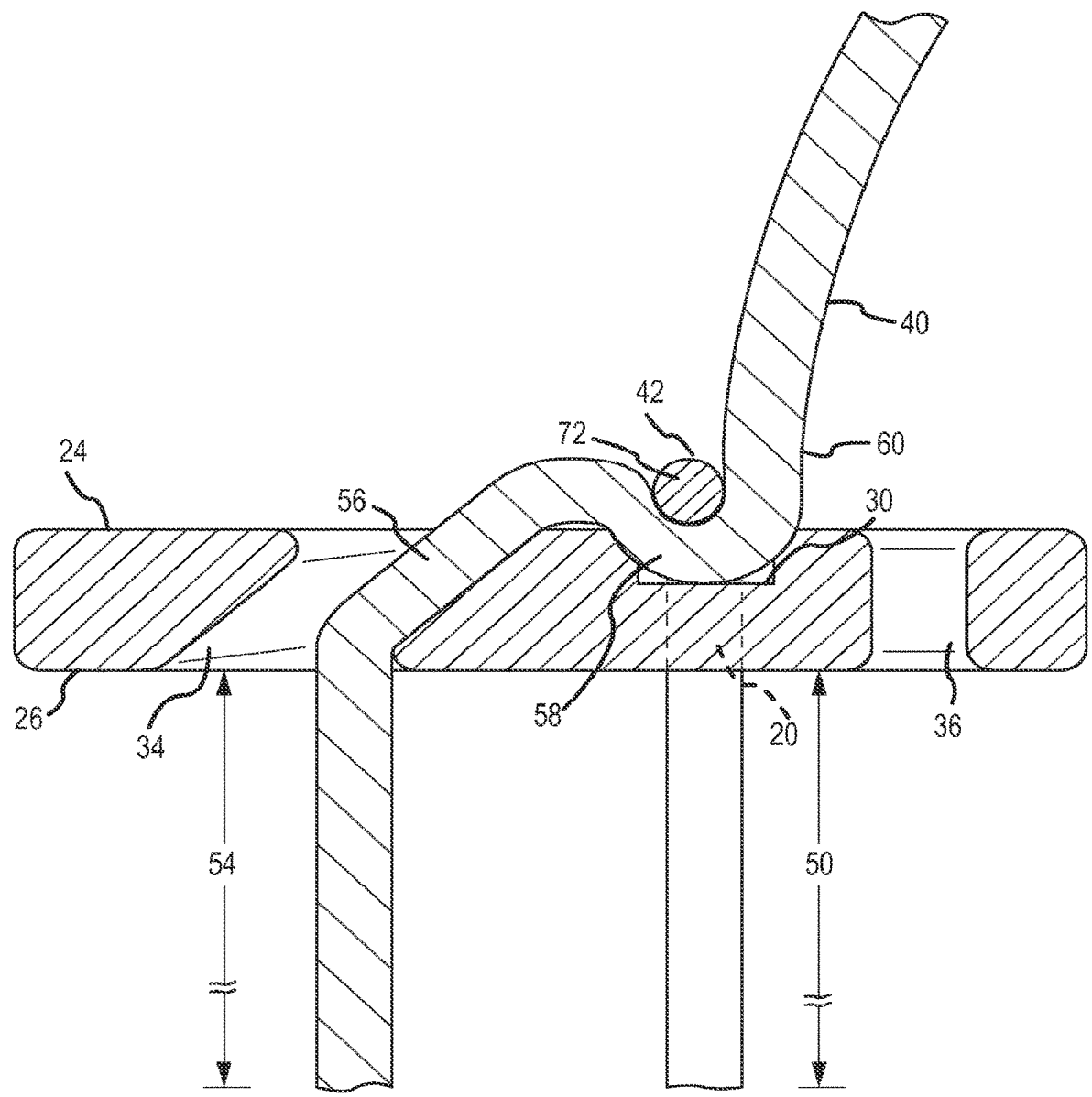
FIG. 4 is a cross-sectional view of the suspensory graft fixation device of FIG. 3 showing the winding path of suture.

Adjustability of the loop length L is achieved by simply pulling on the filament limbs 44 and 46 in section 60 in a distal direction away from anchor member 12. This type of action simultaneously decreases the size/length of the supporting loop and releases the pressure being applied by locking loop 72. When the desired size/length of the supporting loop is achieved, tension is placed on the graft supporting loop 70 in the opposite, proximal direction so the locking loop 72 automatically squeezes the suture limbs securely against anchor member 12 to lock the suture limbs in place. The locking of the graft supporting loop 70 is achieved due to the friction imparted on the filament ends by the locking loop 72. As best seen in FIGS. 1 and 4, aperture 34 is angled relative to surfaces 24 and 26, and inclined toward apertures 20 and 22. This arrangement has been found to enhance the friction between the suture and the surfaces and edges of the anchor member 12.

While the path of the preferred embodiment of device 10 is as shown above, alternate embodiments are feasible. Thus, while the suture path through anchor member 12 results in device 10 comprising a graft supporting element in the form of the aforementioned graft supporting loop member 70 suspended from anchor member 12, alternate embodiments of device 10 are feasible in which bridge 28 between suture receiving apertures 20 and 22, is formed by a transverse pin in the middle of a single opening (not shown). Such a structure would form a bridge and a pair of apertures on either side of the pin.

Figure 2:
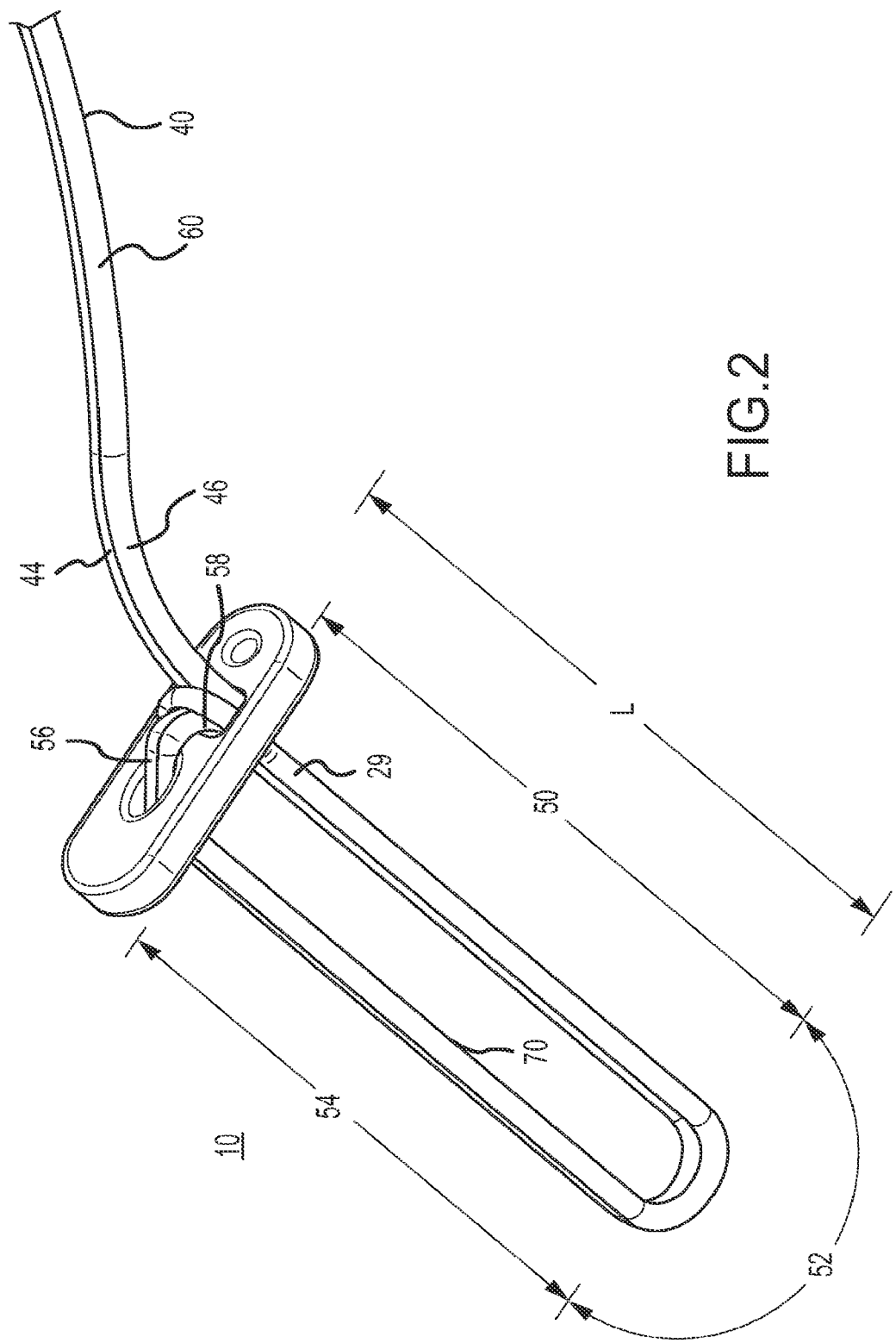
FIG. 2 is a view of the anchor portion of the suspensory graft fixation device of FIG. 1 showing its engagement with a filamentous material such as suture.

Another alternate embodiment could comprise a different loop construction than that described above. As shown in FIGS. 2 through 4, loop member 70 is formed from a single length of suture or other filamentous material 40. In an alternate embodiment the loop could be formed by a plurality of individual suture loops (not shown) which together form graft supporting loop 70. In yet another alternate embodiment loop 70 may be made to pass through an optional slidable flexible cylindrical sleeve 40 (not shown) situated at the section 52 side of the supporting loop, opposite anchor member 12.

In yet another alternate embodiment, in order to facilitate orienting elongated anchor member 12 parallel to the bone tunnel axis and pulling it through the bone tunnel, an optional pulling-suture aperture 36 may be formed at the leading end of the member 12.

In operation, device 10 serves to enable adjustment of loop length L while also producing a relatively large graft fixation force. An advantage of this invention is its ability to provide graft fixation in bone tunnels shorter than those required for prior art suspensory graft repairs. This invention is particularly useful for suspensory type repairs of the ACL or PCL in situations where the bone tunnel length is relatively short. For example, to perform an ACL surgery using a conventional transverse button on the lateral femoral surface, the surgeon must drill a trans-femoral tunnel comprising a proximal graft receiving portion and a smaller diameter distal portion having an opening at the bone tunnel exit onto the lateral femoral cortex. The surgeon must then precisely measure the overall tunnel length and determine the graft tunnel-contact length desired as well as the loop length required to achieve the desired contact between the tunnel wall and the graft. The surgeon then calculates the drilling length of the graft tunnel socket by selecting the length of graft desired to remain in the tunnel and, in the case of a button with a continuous (i.e., endless) non-adjustable graft retaining loop, adding the distance needed to deploy (i.e., flip) the button. The reason the added distance is necessary is because the button must completely exit the aperture prior to toggling perpendicular to the exit hole. This in turn requires the graft to be pulled deeper into the bone tunnel, possibly even momentarily contacting the floor (end) of the socket. When this happens the button can flip into a transverse orientation and when it is then seated against the lateral femur the graft will pull back from the socket floor, thereby leaving a gap between the socket floor and the graft. A typical example of this would be a situation where there is an overall trans-femoral tunnel length of 45 mm and where 20 mm of graft is desired to remain in the tunnel and 15 mm is needed to deploy the button. In this case the surgeon would drill the proximal (main) portion of the femoral socket 35 mm deep. Once the procedure is completed there will be excess space present between the femoral socket floor and the distal end of the graft. At this point, if one were using conventional non-adjustable techniques and devices, the graft would be in its final position, that is, with a space between the graft and the socket floor.

On the other hand, as will be understood below, use of the subject invention enables the advantageous elimination of this excess space and the maximization of graft contact with the bone tunnel wall where short trans-femoral tunnels are desired or encountered. That is, the method of ACL repair using the subject invention does not require a permanent, empty extra tunnel length to enable the button to turn.

The invention allows the graft retaining loop 70 to be sufficiently long so that the button may be passed through the femoral tunnel and deployed on the surface of the bone no matter how long the loop length is. For example, the loop length can be made long enough to enable the saddle portion of the supporting loop to be accessible from inside the joint and outside the femoral tunnel so that the saddle portion of the graft supporting loop 70 may be engaged by the graft ligament (folded about loop 70) even after the button has been flipped. The graft ligament, thus supported directly by the plurality of individual loops making up loop 70, is then pulled into the bone tunnel by pulling the suture ends 44 and 46 distally to shorten loop length L. The graft may be thus pulled into the tunnel until it contacts the socket floor. In either case, using this method it would be possible to even load the graft onto the supporting loop outside the joint. Once the graft is in the correct position an optional knot may be tied using limbs 44 and 46 to provide some additional resistance to any tendency of the limbs to pull out from under locking loop 72.

In the preferred embodiment the length of anchor member 12 may range from 12 mm to 20 mm, the diameters of apertures 20 and 22 may be on the order of 1 mm, the pocket/recess 30 may be in the range of 1 mm-2 mm wide and the suture diameter may be on the order of 1 mm or USP size #5.

Figure 5:
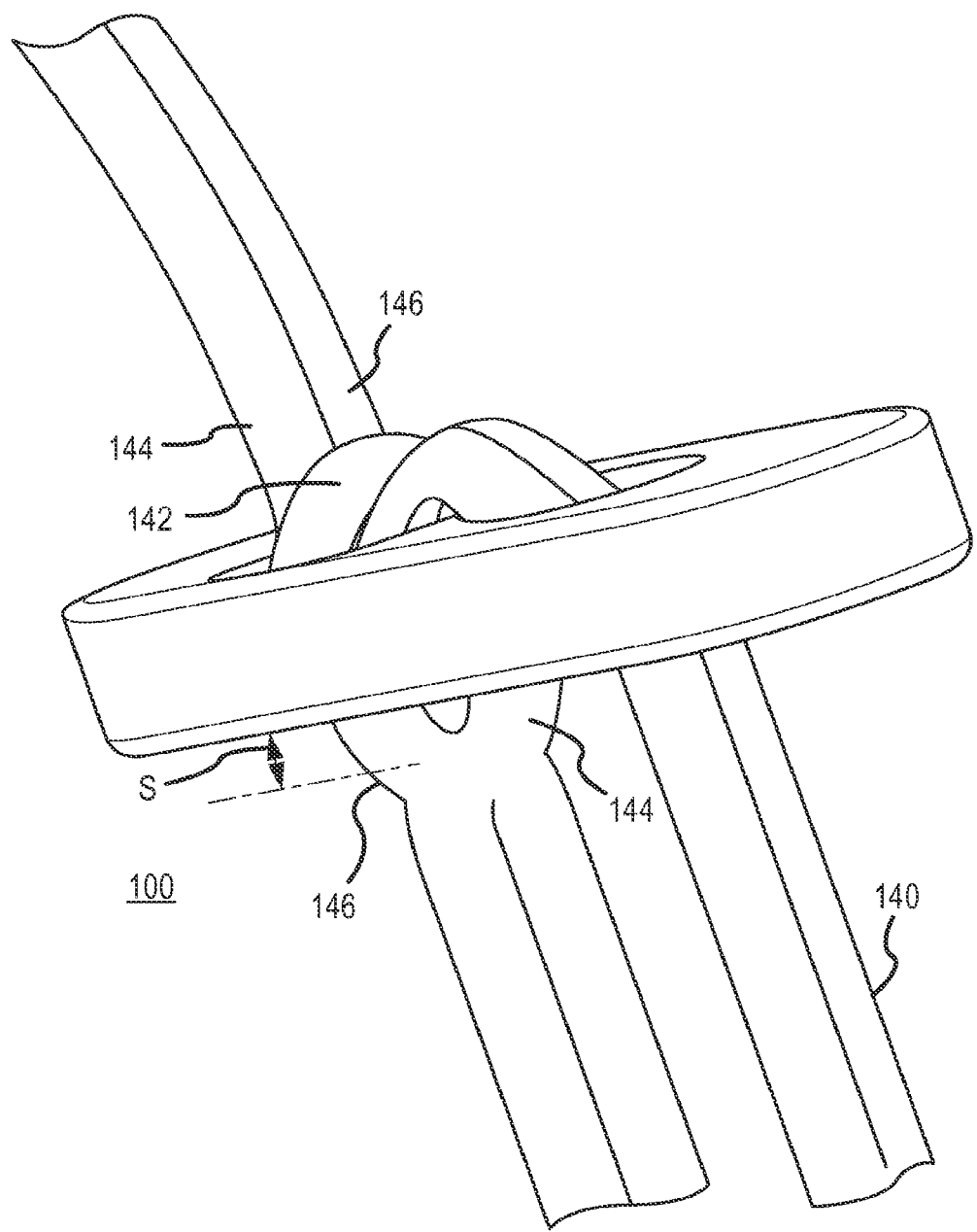
FIG. 5 is a perspective view of an alternate embodiment of a suspensory graft fixation device threaded with a filamentous material.

An alternate embodiment of the invention is shown in FIG. 5 as device 100. Device 100 comprises component parts identical to those of device 10 with the sole exception being that the structure of filamentous strand 140 is modified. That is, strand 140 is folded on itself to produce a bight 142 from which extend two limbs 144 and 146, however, one of these limbs is passed (e.g., via piercing) through the lumen of the other end. Alternatively, as shown in FIG. 5, as the two limbs are threaded through the suture receiving apertures (not seen in FIG. 5), at a point a short distance "S" below the anchor member, limb 144 passes through limb 146 and/or limb 146 passes through limb 144. This has the effect of loosely securing the strand 140 to device 100 to thereby limit travel of the bight 142 when ends 144 and 146 are momentarily pulled distally to resize the graft retaining loop.

Figure 6:
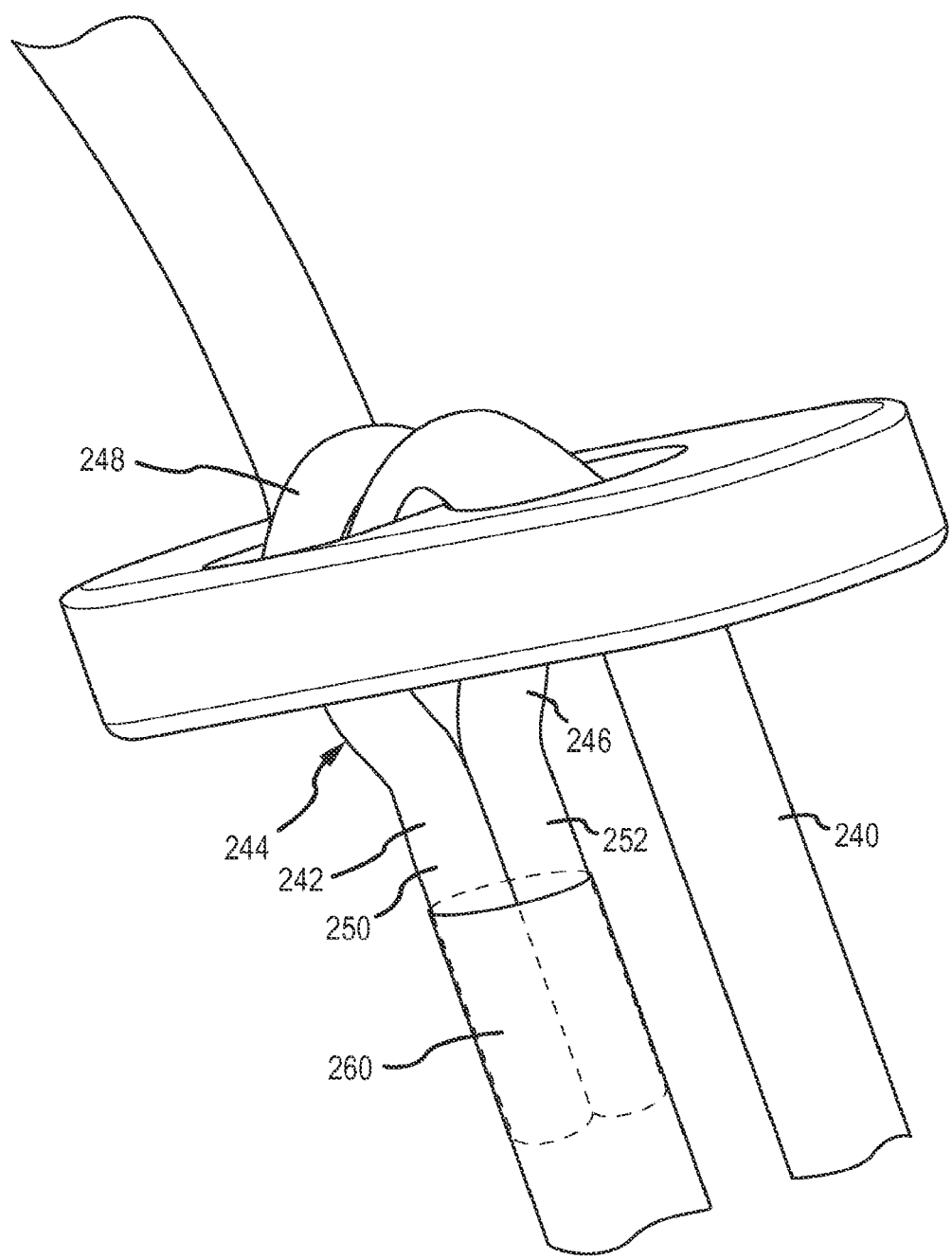
FIG. 6 is a perspective view of an alternate embodiment of a suspensory graft fixation device using a single hollow core suture threaded within the apertures of an anchor member, and a separate bight member.

The use of a single length of filamentous material folded on itself and directed in a winding path facilitates the construction and operation of device 10. In part this is because the bight 42 creates a locking loop 72 due to the passage of the suture limbs 44, 46 under bight 42. It will be understood, however, that an alternate embodiment could be formed from a single strand 240 of a hollow core suture instead of double strands 44, 46, as shown in FIG. 6. In this case, a separate short strand 242 of suture is folded on itself to create a bight element 244 having only a loop 246, creating a locking loop 248, and a pair of very short limbs 250 and 252. The ends of the limbs 250, 252 of the short strand 242 are received a predetermined distance within the lumen 260 of the single hollow core suture 240. It will be understood that this construct operates like a "finger trap" wherein tension on the end of suture 240 will cause it to constrict around legs 250, 252.

It will be understood by those skilled in the art that numerous improvements and modifications may be made to the preferred embodiment of the invention disclosed herein without departing from the spirit and scope thereof

What is claimed is:

1. A suspensory graft fixation device for securing a replacement graft ligament in a bone tunnel comprising:
    an elongated anchor member adapted to be situated transversely adjacent a distal end of said bone tunnel, said elongated anchor member comprising a top surface and a bottom surface, a traverse recessed portion formed on said top surface, a pair of parallel suture receiving apertures located within said traverse recessed portion for receiving a suture passing therethrough in a proximal direction, a bridge portion formed between said pair of parallel suture receiving apertures to suspend and frictionally engage a graft supporting loop element, and a suture return aperture for receiving the suture passing therethrough in a distal direction, wherein the pair of parallel suture receiving apertures and the suture return aperture pass through said anchor member from said top surface to said bottom surface;
    a suture folded on itself to form a bight and a pair of parallel suture limbs extending from said bight, said suture attached to said elongated anchor member and having a proximal end and a distal end, said suture threaded through said apertures along a predetermined path wherein said proximal end of said suture is situated at a point proximal to said anchor member and said distal end of said suture is situated at a point distal to said anchor member, a portion of said predetermined path formed into a graft supporting loop element for connecting said anchor member and said replacement graft ligament, said graft supporting loop element adapted to support said replacement graft ligament in said bone tunnel proximally of said distal end of said bone tunnel and at a selected predetermined distance from said distal end of said bone tunnel;
    means for joining said parallel suture limbs at a point proximal to said anchor member in order to minimize the movement of said suture away from said anchor member, wherein said means for joining said parallel suture limbs at a point proximal to said anchor member is effected by passing at least one suture limb through the other to create a movable junction between said parallel suture limbs; and
    means for automatically locking said graft supporting loop element at said predetermined distance,
    wherein said pair of parallel suture receiving apertures receive said pair of parallel suture limbs, and said bight is situated immediately adjacent said traverse recessed portion of said anchor member,
    wherein said suture return aperture receives said distal end of the suture, and said distal end of the suture passes between said bight and said traverse recessed portion of said anchor member,
    wherein said means for automatically locking is activated by tension applied to said graft supporting loop element in a proximal direction causing the bight to frictionally engage the graft supporting loop between the bight and the traverse recessed portion of the elongated anchor member.

2. A suspensory graft fixation device according to claim 1 further comprising means for adjusting said predetermined distance.

3. A suspensory graft fixation device according to claim 2 wherein said suture is a hollow-core suture.

4. A suspensory graft fixation device according to claim 2 wherein said means for adjusting is activated by moving said distal end of the suture distally relative to said elongated anchor member until said replacement graft ligament is situated at said selected predetermined distance.

* * * * *